(12) United States Patent
Shaw et al.

(10) Patent No.: US 9,247,899 B2
(45) Date of Patent: Feb. 2, 2016

(54) BLOOD DRAW DEVICE WITH RETRACTABLE NEEDLE

(75) Inventors: Thomas J. Shaw, Frisco, TX (US); Mark Small, Leonard, TX (US); Ni Zhu, Plano, TX (US)

(73) Assignee: Retractable Technology, Inc., Little Elm, TX (US)

( * ) Notice: Subject to any disclaimer, the term of this patent is extended or adjusted under 35 U.S.C. 154(b) by 392 days.

(21) Appl. No.: 13/517,465

(22) PCT Filed: Dec. 29, 2010

(86) PCT No.: PCT/US2010/062373
§ 371 (c)(1),
(2), (4) Date: Jun. 20, 2012

(87) PCT Pub. No.: WO2011/100039
PCT Pub. Date: Aug. 18, 2011

(65) Prior Publication Data
US 2012/0259243 A1 Oct. 11, 2012

Related U.S. Application Data

(60) Provisional application No. 61/293,064, filed on Jan. 7, 2010.

(51) Int. Cl.
*A61B 5/00* (2006.01)
*A61B 5/15* (2006.01)
*A61B 5/154* (2006.01)
*A61M 5/32* (2006.01)

(52) U.S. Cl.
CPC ........... *A61B 5/1444* (2013.01); *A61B 5/15003* (2013.01); *A61B 5/154* (2013.01); *A61B 5/150389* (2013.01); *A61B 5/150496* (2013.01); *A61B 5/150572* (2013.01);

(Continued)

(58) Field of Classification Search
CPC . A61B 5/1405; A61B 5/1438; A61B 5/15003
USPC .................................................. 600/573, 576
See application file for complete search history.

(56) References Cited

U.S. PATENT DOCUMENTS 4,747,831 A 5/1988 Kulli
5,195,985 A 3/1993 Hall
(Continued)

FOREIGN PATENT DOCUMENTS

EP 1306097 5/2003

*Primary Examiner* — Sean Dougherty
*Assistant Examiner* — Daniel Cerioni
(74) *Attorney, Agent, or Firm* — Ross Bornes LLP; Monty L. Ross; Robin L. Barnes

(57) ABSTRACT

The Invention comprises a body, an actuator pivotally connected to the body, and a retractable needle adapted to provide fluid communication between a patient and a fluid collection tube, typically a blood collection tube, attachable to the device. A significant feature of the subject device is a retraction cavity disposed inside the actuator that is manually positionable to receive a portion of the needle retraction assembly following removal of the blood collection tube. Retraction is initiated by depressing the forwardly extending end of the actuator relative to the body, thereby causing a retainer clip to release the needle holder, after which the needle holder and a part of the needle are propelled into the retraction cavity by expansion of a compressed spring. The needle is thereby withdrawn from the patient and into the housing, reducing the likelihood of accidental needle sticks and preventing reuse of the device.

9 Claims, 6 Drawing Sheets

(52) U.S. Cl.
CPC .... *A61B 5/150732* (2013.01); *A61B 5/150259* (2013.01); *A61M 5/3232* (2013.01); *A61M 2005/3206* (2013.01)

(56) References Cited

U.S. PATENT DOCUMENTS

| | | | |
|---|---|---|---|
| 6,004,278 A * | 12/1999 | Botich et al. | 600/576 |
| 6,524,276 B1 * | 2/2003 | Halseth et al. | 604/110 |
| 7,056,306 B1 | 6/2006 | Halseth et al. | |
| 7,803,123 B2 * | 9/2010 | Perez et al. | 600/583 |
| 2005/0101881 A1 | 5/2005 | Shue et al. | |
| 2005/0101914 A1 | 5/2005 | Shue et al. | |
| 2006/0079807 A1 | 4/2006 | Allard | |
| 2006/0079808 A1 | 4/2006 | Allard | |
| 2006/0079847 A1 * | 4/2006 | Crawford | 604/192 |
| 2009/0306601 A1 | 12/2009 | Shaw et al. | |

\* cited by examiner

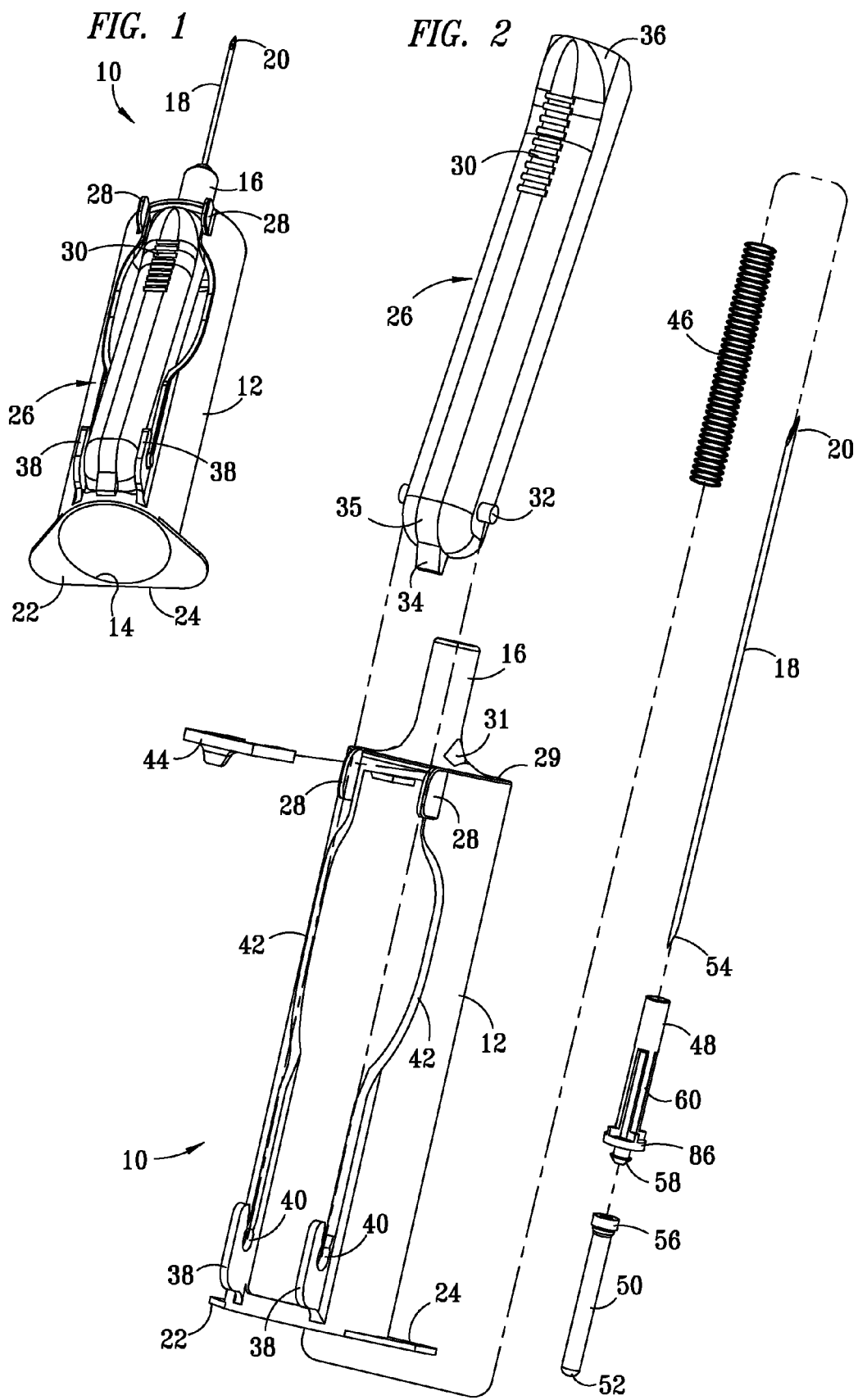

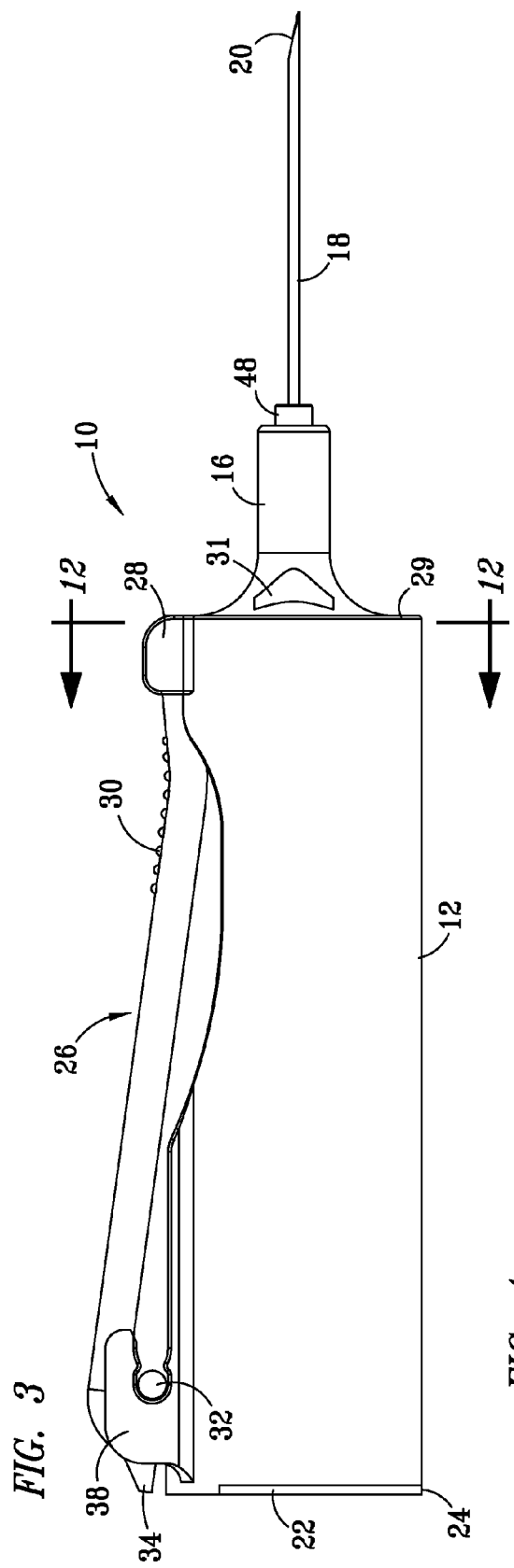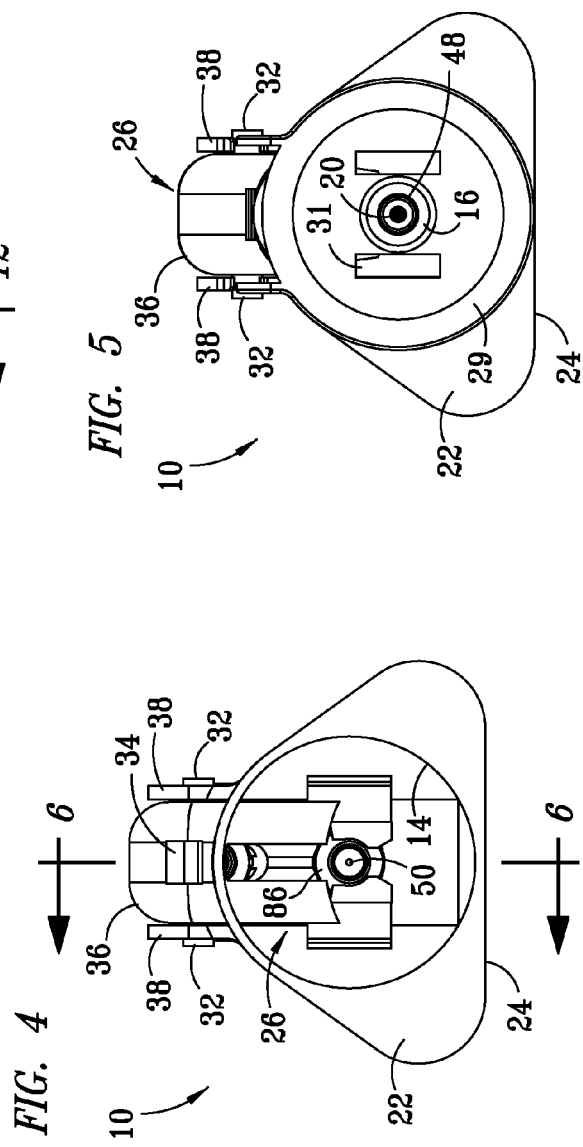

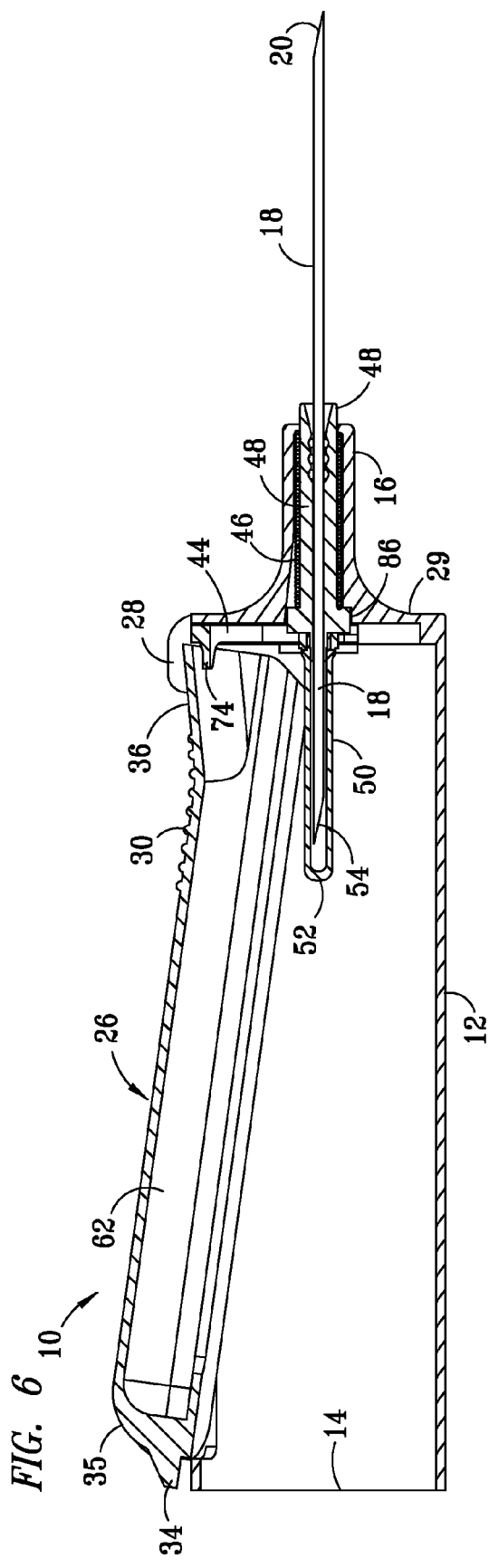
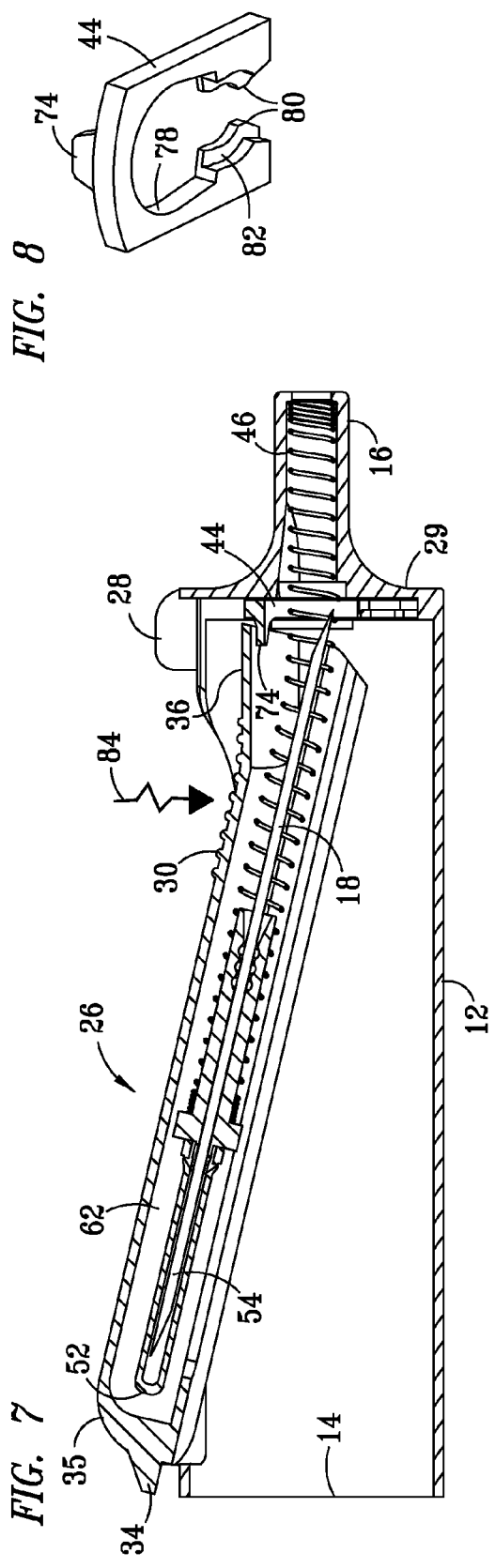
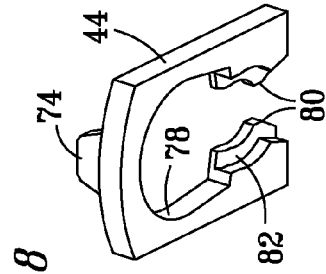

US 9,247,899 B2

BLOOD DRAW DEVICE WITH RETRACTABLE NEEDLE

TECHNICAL FIELD OF THE INVENTION

This invention relates to a medical device that is useful for safely drawing blood from a patient and is, according to one embodiment, a blood collection tube holder that can be used in cooperation with a conventional blood collection tube.

SUMMARY OF THE INVENTION

One preferred device of the invention comprises a body, an actuator pivotally connected to the body, and a retractable needle adapted to provide fluid communication between a patient and a fluid collection tube, typically a blood collection tube, attachable to the device. A significant feature of the subject device is a retraction cavity disposed inside the actuator that is manually positionable to receive a portion of the needle retraction assembly following removal of the blood collection tube. Retraction is initiated by depressing the forwardly extending end of the actuator relative to the body, thereby causing a retainer clip to release the needle holder, after which the needle holder and a part of the needle are propelled into the retraction cavity by expansion of a compressed spring. The needle is thereby withdrawn from the patient and into the housing, reducing the likelihood of accidental needle sticks and preventing reuse of the device or any associated contamination by blood-borne pathogens.

BRIEF DESCRIPTION OF THE DRAWINGS

One preferred medical device of the invention is further described and explained in relation to the following FIGURES of the drawings, wherein:

FIG. 1 is a top perspective view of the medical device of the invention;

FIG. 2 is an exploded perspective view of the medical device of FIG. 1;

FIG. 3 is a side elevation view of the medical device of FIG. 1;

FIG. 4 is a rear elevation view of the medical device of FIG. 1;

FIG. 5 is a front elevation view of the medical device of FIG. 1;

FIG. 6 is a cross-sectional elevation view taken along line 6-6 of FIG. 4;

FIG. 7 is a cross-sectional elevation view of the medical device of FIG. 6 after the needle has been retracted by depressing the front end of the actuator relative to the body;

FIG. 8 is an enlarged top front perspective view of the retainer clip of FIG. 2;

DESCRIPTION OF A PREFERRED EMBODIMENT

Figure 9:
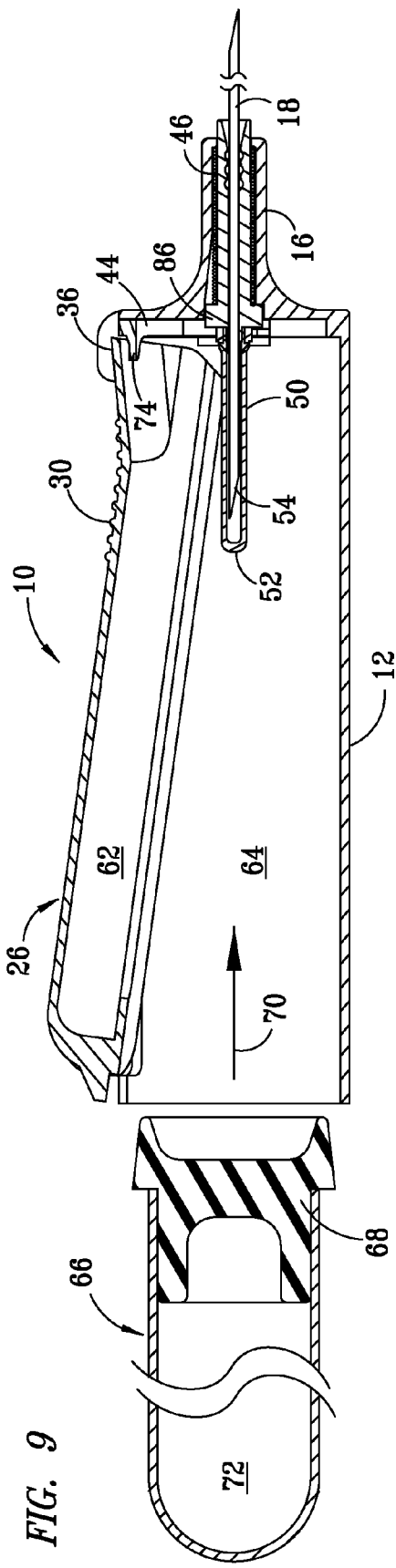
FIG. 9 is a cross-sectional view as in FIG. 6, but showing a conventional blood collection tube being inserted into the medical device of the invention.

Referring to FIGS. 1-6, device 10 comprises body 12 with substantially cylindrical rear opening 14, forwardly extending nose 16, laterally extending stabilizing flanges 22 defining in part a substantially flat bottom 24 that cooperates with stabilizing flanges 22 to prevent device 10 from rolling when positioned on an underlying support surface. Actuator 26 is pivotally mounted relative to body 12. The portion of body 12 disposed between nose 16 and stabilizing flanges 22 is substantially tubular but has an upwardly facing slot 42 sufficiently large to permit the forwardly extending portion of actuator 26 to pivot upwardly and downwardly relative to body 12 during use as further described below. Retainer clips 38 disposed adjacent each side of upwardly facing slot 42 near the rear of body 12 are provided to receive and support bosses 32 projecting laterally from each side of actuator 26. Rearwardly extending tab 34 on actuator 26 is provided to limit the distance that rear 35 of actuator 26 can pivot relative to the rear of body 12.

Actuator 26 further comprises a front end 36 and a series of parallel transverse ridges that serve as a finger pad 30 for the application of manual pressure downwardly against the top front surface of actuator 26 as described below. It will be apparent, however, that other forms of surface texturing can be similarly effective for use as finger pad 30. Actuator 26 also comprises a longitudinally extending retraction cavity 62 with an open front end. The length and transverse dimensions of retraction cavity 62 are desirably large enough to facilitate retraction of forwardly extending needle 18 as described below.

Needle 18 comprises forwardly extending bevel 20, rearwardly extending bevel 54, and extends through needle holder 48. Needle 18 is held in fixed axial relation to needle holder 48 by any suitable means, such as glue. Needle holder 48 is substantially tubular but comprises a larger diameter head portion 86 disposed near its rearwardly facing end. Spring 46 is desirably seated on an annular shoulder and is compressed inside the front of nose 16 of body 12. Spring 46 surrounds stem 60 of needle holder 48, and the rearwardly facing end of spring 46 desirably has an outside diameter that is slightly less than the outside diameter of head 86 of needle holder 48 so that the rearwardly facing end of spring 46 is constrained by head 86.

A flexible polymeric sheath 50 comprising a forwardly facing collar 56 provides frictional engagement with rearwardly projecting tubular boss 58 at the rear of needle holder 48. Polymeric sheath 50 is desirably long enough to extend slightly beyond rear bevel 54 of needle 18 when needle 18 is affixed inside needle holder 48, but is thin enough that closed end 52 will slide rearwardly and be pierced by bevel 54 when contacted by stopper 68 in the forwardly extending end of blood tube holder 66 as described below in relation to FIGS. 9 and 10. Body 12, actuator 26 and needle holder 48 are all desirably made of moldable polymeric resins, preferably comprising polypropylene. Polymeric sheath 50 is desirably made of a rubbery, elastomeric material.

During assembly of device 10, sheath 50 is desirably attached to needle holder 48 and spring 46 is desirably placed over stem 60 of needle holder 48 and then compressed as spring 46 and needle holder 48 are inserted into nose 16 of body 12. While spring 46 is being held in its compressed position, retainer clip 44, better seen in FIG. 8, is inserted transversely through slot 42 to a position where it snaps onto head 86 of needle holder 48 and head 86 of needle holder 48 is captured inside recess 82 adjacent to a notch formed by opposed arms 80 of retainer clip 44. Retainer clip 44 resists the force exerted on head 86 of needle holder 48 until retainer clip 44 is repositioned as discussed in relation to FIG. 7 below to initiate retraction. Needle 18 can be inserted into and attached to needle holder 48 prior to insertion of needle holder 48 into nose 16 of body 12, or can be inserted into the forwardly extending end of needle holder 48 afterwards if desired. In either case, needle holder 48, spring 46 and retainer clip 44 are collectively referred to as the retraction assembly.

Following installation of the retraction assembly inside body 12, actuator 26 is desirably attached to body 12 as shown in FIGS. 3 and 6, with the rear end of actuator 26 being pivotably connected to body 12 and with front lip 36 of actuator 26 resting on rearwardly extending tab 74 of retainer clip 44. Although not shown in the drawings, it should be appreciated that needle 18 of device 10 as shown in FIG. 3 will desirably be covered with a needle cover that frictionally engages nose 16 of body 12, packaged and sterilized prior to shipment.

A preferred use of device 10 is further described in relation to FIGS. 7-13. First referring to FIG. 9, a conventional blood collection tube 66 having one closed end and one open end containing rubber stopper 68 is inserted into opening 14 (FIG. 7) at the rear end of body 12. Blood collection tube 66 defines an interior cavity 72 that is desirably partially evacuated to a pressure less than atmospheric to facilitate the introduction of blood into the cavity. As blood collection tube 66 is advanced forwardly inside interior space 64 of body 12 as indicated by arrow 70, the underside of actuator 26 rides on the top of blood collection tube 66, and the front portion of actuator 26 is elevated to the position shown in FIG. 10. In this position, the underside of front lip 36 of actuator 26 is disposed well above rearwardly extending tab 74 of retainer clip 44.

Figure 10:
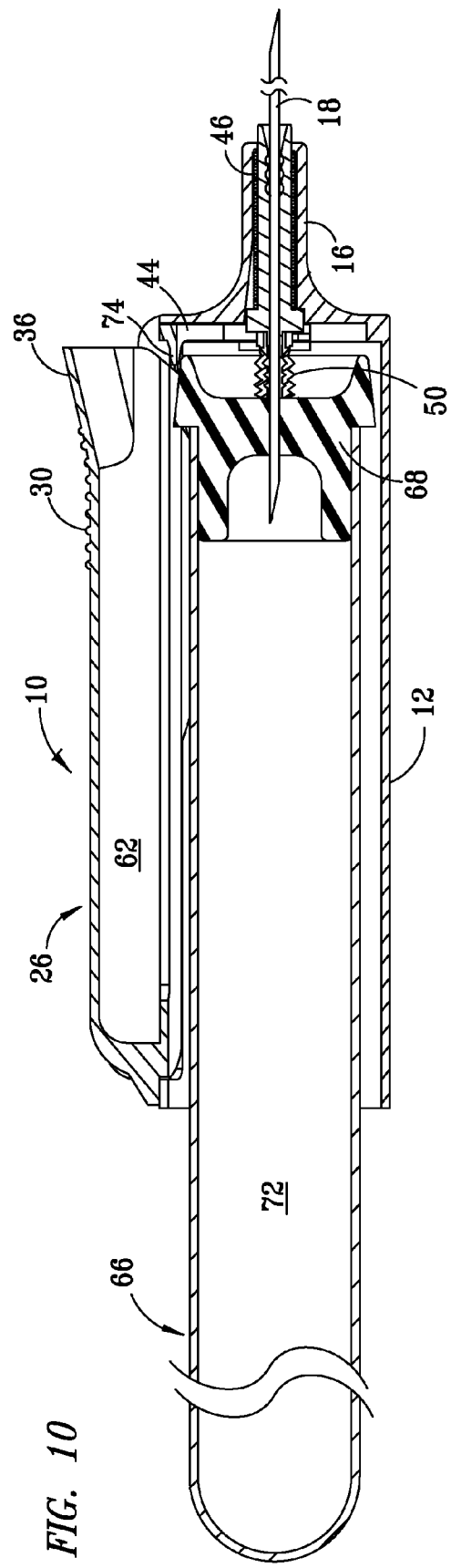
FIG. 10 is a cross-sectional view as in FIG. 9, but showing the blood collection tube fully inserted into the body and the actuator elevated to its uppermost position relative to the body.

As stopper 68 of blood collection tube 66 contacts end 52 of sheath 50, end 52 is pushed backward until it is perforated by bevel 54 (FIG. 9) of needle 18, which then penetrates stopper 68 until it extends into cavity 72 of tube 66. As stopper 68 approaches front end wall 29 (FIG. 7) of body 12, sheath 50 is crumpled into the void between stopper 68 and body 12 as shown in FIG. 10, and remains in that position during use of device 10. While configured as shown in FIG. 10, front bevel 20 of needle 18 is inserted into a patient, and blood or other bodily fluid is withdrawn through needle 18 into cavity 72 of tube 66. In some cases, after tube 66 is filled to a desired level, it is removed an another blood collection tube 66 is similarly installed inside the same device 10. As each blood collection tube 66 is withdrawn from body 12, front end 36 of actuator 26 again drops to its resting position as shown in FIG. 6.

Figure 11:
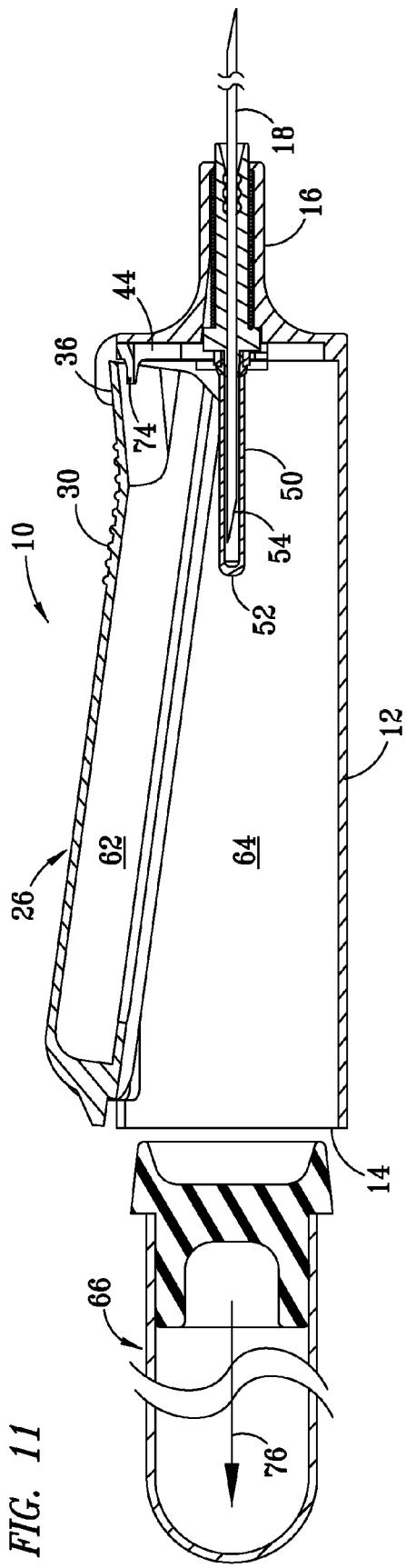
FIG. 11 is a cross-section view as in FIG. 10, but showing the blood collection tube as it is removed from the body and the actuator returned to its pre-use position as shown in FIG. 6.
Figure 12:
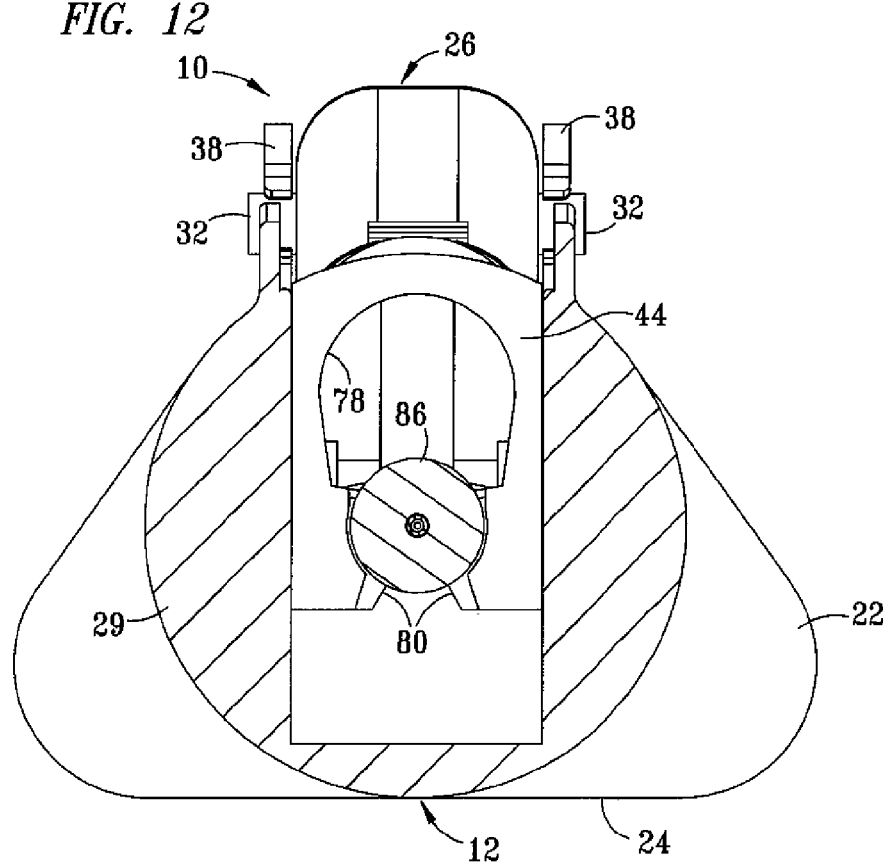
FIG. 12 is an enlarged cross-sectional elevation view taken along line 12-12 of FIG. 3, showing the subject medical device in its pre-use position.
Figure 13:
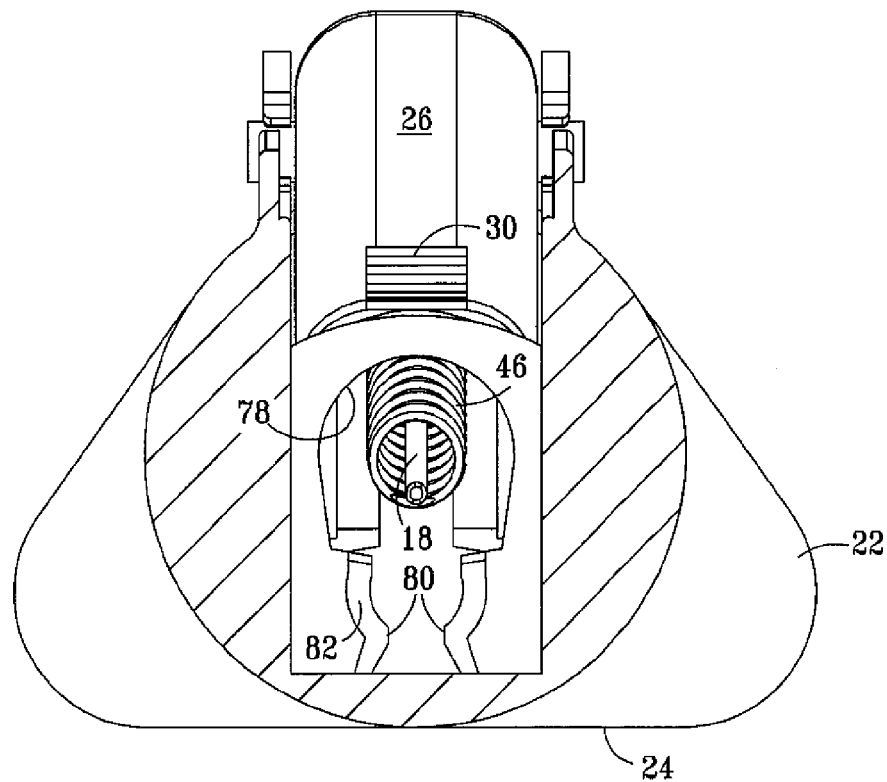
FIG. 13 is an enlarged cross-sectional elevation view taken at the same position as in FIG. 12, but showing the subject medical device following retraction of the needle.

Once the total desired amount of bodily fluid has been withdrawn from the patient using device 10, the last blood collection tube 66 to be filled is withdrawn from body 12 as indicated by arrow 76 in FIG. 11, whereupon end 52 of sheath 50 again expands until it covers bevel 54 of needle 18. Needle 18 can then be retracted from its forwardly projecting position by initiating the retraction sequence. Referring to FIGS. 7-13, manual pressure is desirably exerted downwardly against finger pad 30 as indicated by arrow 84. As front end 36 of actuator 26 is depressed, it contacts rearwardly extending tab 74 of retainer clip 44. The continued application of manual force to finger pad 30 causes retainer clip 44 to move downwardly to a position where head 86 of needle holder 48 is inside larger aperture 78 and is no longer captured in recess 82 between opposed arms 80. When this occurs, there is no longer any restraining force to overcome the rearwardly directed biasing force of compressed spring 46, and spring 46 drives sheath 50, needle holder 48 and the rearwardly extending portions of spring 46 rearwardly into retraction cavity 62 inside actuator 26 as shown in FIG. 7. When the retraction assembly is positioned as shown in FIG. 7, both ends of needle 18 are fully protected inside either actuator 26 or body 12. Moreover, the uncompressed spring continues to exert tension against needle holder 48 to maintain actuator 26 in that position relative to body 12 pending disposal of device 10.

Other alterations and modifications of the device disclosed herein will likewise become apparent to those of ordinary skill in the art upon reading this disclosure in relation to the accompanying drawings, and it is intended that the scope of the invention be limited only by the broadest interpretation of any appended claims to which the inventors are legally entitled.

The invention claimed is:

1. A medical device adapted for use as a holder for a blood collection tube, comprising:
    a body having a substantially cylindrical rear opening, a forwardly extending nose, laterally extending stabilizing flanges disposed adjacent to the cylindrical rear opening, and an upwardly facing slot disposed between the nose and the stabilizing flanges;
    an actuator pivotably mounted relative to the body by opposed first and second retainer clips disposed adjacent to the slot near the rear of the body that receive and support bosses projecting laterally from each side of a rear portion of the actuator, the actuator comprising a longitudinally extending retraction cavity with an open front end that can pivot downwardly into the upwardly facing slot, the slot being sufficiently large to permit the front end of the actuator to pivot upwardly and downwardly relative to the body during use;
    a retractable needle having an unretracted position projecting forwardly beyond the body and a retracted position disposed inside the body and retraction cavity; and
    a retraction assembly comprising a needle holder with a stem and a head, a spring, and a third retainer clip, wherein the retractable needle is held in fixed relation to the needle holder, and the spring is initially seated inside the nose and is compressed by the needle holder and held in a compressed position inside the nose by the needle holder and by the third retainer clip to maintain the retractable needle in the unretracted position prior to and during use of the medical device to collect blood;
    and wherein the retractable needle is retractable following the collection of blood by applying manual force to the actuator to pivot the actuator downwardly into the upwardly facing slot, thereby contacting and causing the third retainer clip to move downwardly and release the needle holder, after which the needle holder and a part of the retractable needle are driven into the retraction cavity by expansion of the compressed spring to move the retractable needle into the retracted position.

2. The medical device of claim 1 wherein the laterally extending stabilizing flanges define in part a substantially flat bottom that cooperates with the stabilizing flanges to prevent the medical device from rolling.

3. The medical device of claim 1 wherein the actuator further comprises a rearwardly extending tab limiting a distance that the rear portion of the actuator can pivot relative to the rear of the body.

4. The medical device of claim 1 wherein the actuator comprises a top front surface having a textured finger pad adjacent to the open front end for the application of manual pressure downwardly against the top front surface.

5. The medical device of claim 1 wherein the retractable needle comprises oppositely directed beveled ends.

6. The medical device of claim 5 wherein one of the oppositely directed beveled ends is directed rearwardly and is covered by a flexible polymeric sheath until a blood tube holder is inserted into the medical device and engages the rearwardly directed beveled end of the retractable needle.

7. The medical device of claim 6 wherein the flexible polymeric sheath comprises a forwardly facing collar that frictionally engages a rearwardly projecting tubular boss of the needle holder.

8. A medical device adapted for use as a holder for a blood collection tube, comprising:
- a body having a substantially cylindrical rear opening, a forwardly extending nose, laterally extending stabilizing flanges disposed adjacent to the cylindrical rear opening, and an upwardly facing slot disposed between the nose and the stabilizing flanges;
- an actuator pivotably mounted relative to the body by opposed first and second retainer clips disposed adjacent to the slot near the rear of the body that receive and support bosses projecting laterally from each side of a rear portion of the actuator, the actuator comprising a longitudinally extending retraction cavity with an open front end that can pivot downwardly into the upwardly facing slot, the slot being sufficiently large to permit the front end of the actuator to pivot upwardly and downwardly relative to the body during use;
- a retractable needle having an unretracted position projecting forwardly beyond the body and a retracted position disposed inside the body and retraction cavity; and
- a retraction assembly comprising a needle holder with a stem and a head, a spring, and a third retainer clip; wherein the retractable needle is held in fixed relation to the needle holder, and the spring is initially seated inside the nose and is compressed by the needle holder and held in a compressed position inside the nose by the needle holder and by the third retainer clip to maintain the retractable needle in the unretracted position prior to and during use of the medical device to collect blood;
- and wherein the retractable needle is retractable following the collection of blood by applying manual force to the actuator to pivot the actuator downwardly into the upwardly facing slot, thereby contacting and causing the third retainer clip to move downwardly and release the needle holder, after which the needle holder and a part of the retractable needle are driven into the retraction cavity by expansion of the compressed spring to move the retractable needle into the retracted position;
- wherein the third retainer clip comprises opposed arms defining an aperture with an open end and a closed end, a notch formed between the opposed arms, a recess in the opposed arms that is configured to snap onto the head of the needle holder when the retractable needle is in the unretracted position, and a rearwardly extending tab that is contacted by the actuator and moved downwardly relative to the head of the needle holder to initiate retraction of the retractable needle to the retracted position.

9. The medical device of claim 8 wherein the aperture has a portion that is larger than the head of the needle holder.

\* \* \* \* \*